(12) United States Patent
Mayenberger et al.

(10) Patent No.: US 7,963,192 B2
(45) Date of Patent: Jun. 21, 2011

(54) SURGICAL SCISSORS AND METHOD FOR THE MANUFACTURE OF SURGICAL SCISSORS

(75) Inventors: Rupert Mayenberger, Rielasingen (DE); Pedro Morales, Tuttlingen (DE); Dieter Weisshaupt, Immendingen (DE); Richard Zeller, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 1519 days.

(21) Appl. No.: 11/253,284

(22) Filed: Oct. 18, 2005

(65) Prior Publication Data
US 2006/0095060 A1    May 4, 2006

(30) Foreign Application Priority Data
Oct. 22, 2004   (DE) .......................... 10 2004 052 515

(51) Int. Cl.
*B26B 13/28* (2006.01)
*A61B 17/32* (2006.01)
(52) U.S. Cl. ......................... 76/106.5; 30/254
(58) Field of Classification Search ............... 30/254, 30/350; 76/104.1, 106.5
See application file for complete search history.

(56) References Cited

U.S. PATENT DOCUMENTS

| | | | |
|---|---|---|---|
| D53,606 S | 7/1919 | Rauh | |
| D137,412 S | 3/1944 | Storz | |
| 2,725,629 A | 12/1955 | Todhunter | |
| D183,391 S | 8/1958 | Kaplan | |
| D206,311 S | 11/1966 | Eizenberg | |
| 4,285,344 A | 8/1981 | Marshall | |
| 4,428,260 A * | 1/1984 | Eby | 76/104.1 |
| D281,104 S | 10/1985 | Davison | |
| 4,600,007 A | 7/1986 | Lahodny et al. | |
| 4,762,028 A | 8/1988 | Regan | |
| 5,152,774 A | 10/1992 | Schroeder | |
| 5,312,434 A | 5/1994 | Crainich | |
| 5,679,448 A | 10/1997 | Kawata | |
| 5,833,703 A | 11/1998 | Manushakian | |

(Continued)

FOREIGN PATENT DOCUMENTS

DE   39 18 562   12/1990

(Continued)

OTHER PUBLICATIONS

"Item No. DO88 Dovo (Solingen) 3.5" Mustache Scissors, 3.5" Mustache Scissors, high carbon with black oxide coating", 3pp including 2pp of photos, (online), URL:www.web.archive.org/web/20021207043837/http://www.excaliburcutlery.com/scissors5.html, posted Dec. 7, 2002.

(Continued)

*Primary Examiner* — Stephen Choi
(74) *Attorney, Agent, or Firm* — Lipsitz & McAllister, LLC

(57) ABSTRACT

Surgical scissors are provided having two scissor blades mounted for pivotal movement relative to each other about a pivot axis and having one cutting edge each. The scissor blades have, proximal of the pivot axis, one sliding surface area each, the sliding surface areas sliding along each other and the scissor blades contacting each other distally of the pivot axis at a moving point of contact of the cutting edges sliding along each other when the scissors are opened and closed. At least one of the cutting edges is provided with a hard material coating, and at least one of the two sliding surface areas have a first hard material coating-free surface. A method for the manufacture of surgical scissors is also proposed.

14 Claims, 4 Drawing Sheets

U.S. PATENT DOCUMENTS

| | | | |
|---|---|---|---|
| 6,060,695 | A | 5/2000 | Harle et al. |
| 6,988,318 | B2 * | 1/2006 | Buchtmann et al. ............ 30/350 |
| 2003/0229371 | A1 | 12/2003 | Whitworth |
| 2004/0133989 | A1 * | 7/2004 | Lombardi et al. ................ 7/129 |
| 2004/0144318 | A1 | 7/2004 | Beck et al. |
| 2004/0193200 | A1 | 9/2004 | Dworschak et al. |
| 2005/0203556 | A1 | 9/2005 | Olsen |
| 2005/0241440 | A1 * | 11/2005 | Beck ............................ 76/106.5 |
| 2006/0095060 | A1 | 5/2006 | Mayenberger et al. |

FOREIGN PATENT DOCUMENTS

| | | | |
|---|---|---|---|
| DE | 41 05 582 | | 8/1992 |
| DE | 44 08 250 | | 1/1995 |
| DE | 101 04 611 | | 8/2002 |
| JP | 63210266 | * | 8/1988 |
| WO | DM/053545 | | 10/2000 |
| WO | DM/057244 | | 7/2001 |
| WO | DM/060539 | | 7/2002 |
| WO | DM/062897 | | 12/2002 |
| WO | DM/062884 | | 2/2003 |

OTHER PUBLICATIONS

"Item No. DO005 Dovo (Solingen) 5.5" Styling Shears Hot forged, brushed stainless cushioned finger ring, removable finger rest", 3pp including 2pp of photos, (online), URL:www.web.archive.org/web/20021207043837/http://www.excaliburcutlery.com/scissors5.html, posted Dec. 7, 2002.

Zimmer, "Metzenbaum Dissecting Scissors" Nov. 1997, Zimmer Product Catalog, pp. 320.

Sklar, J., "T-C needle holders" Jul. 9, 1984, J. Sklar Mfg. Co., Inc. 20$^{th}$ Edition, pp. 98-101.

Charrette, Art, Architectural, Office, Computer, Drafting and Design Supplies and Equipment, Summer 1990, pp. Cover, Lower right corner.

Simmons Hardware Company, "Shears, Barbers' Keen Kutter—French Pattern No. K128/71/2& Bay State, Straight Trimmers No. 50/7", Catalog No. U, May 7, 1936, pp. 1413.

* cited by examiner

SURGICAL SCISSORS AND METHOD FOR THE MANUFACTURE OF SURGICAL SCISSORS

The present disclosure relates to the subject matter disclosed in German application number 10 2004 052 515.3 of Oct. 22, 2004, which is incorporated herein by reference in its entirety and for all purposes.

BACKGROUND OF THE INVENTION

The present invention relates to surgical scissors with two scissor blades mounted for pivotal movement relative to each other about a pivot axis and having one cutting edge each, the scissor blades having proximally of the pivot axis one sliding surface area each, the sliding surface areas sliding along each other and the scissor blades contacting each other distally of the pivot axis at a moving point of contact of the cutting edges sliding along each other when the scissors are opened and closed, and at least one of the cutting edges being provided with a hard material coating.

The present invention further relates to a method for the manufacture of surgical scissors with two scissor blades mounted for pivotal movement relative to each other about a pivot axis and having one cutting edge each, the scissor blades having proximally of the pivot axis one sliding surface area each, the sliding surface areas sliding along each other and the scissor blades contacting each other distally of the pivot axis at a moving point of contact of the cutting edges sliding along each other when the scissors are opened and closed, and at least one of the cutting edges being provided with a hard material coating.

A hard material coating within the meaning of this application is to be understood as a coating whose hardness is significantly increased in comparison with a base material forming the scissor blades. It is not to be understood as ceramic coating or coating applied by welding.

Surgical scissors of the kind described at the outset are used in order to increase a service life of the scissors in comparison with uncoated scissors. This is achieved, in particular, by at least one of the cutting edges being provided with a single-layer or multi-layer hard material coating, applied, for example, by chemical vapor deposition (CVD). In particular, titanium-nitride can be applied in a vacuum chamber by evaporating titanium in a nitrogen plasma. Of course, both cutting edges may also be provided with a hard material coating.

Furthermore, it is known that the scissor blades mounted on each other under initial tension contact each other at at least two points or areas when the scissors are opened and closed. These are, firstly, a moving point of contact of the cutting blades sliding along each other and, secondly, a point of contact or a contact surface of the sliding surface areas of the two scissor blades that slide along each other. The initial tension between the scissor blades required for the cutting can only be maintained on a long-term basis if not only wear at the cutting edges is minimized but also wear at the sliding surface areas that slide along each other.

The object of the present invention is, therefore, to so improve surgical scissors of the kind described at the outset that their service life is further increased.

SUMMARY OF THE INVENTION

This object is accomplished with surgical scissors of the kind described at the outset, in accordance with the invention, in that at least one of the two sliding surface areas has a first hard material coating-free surface.

Owing to this special type of coating, in particular, in the case of scissors provided completely with a hard material coating, the applied particles of the coating, when attacked, for example, by chemicals, are prevented from mutually acting as abrasive agents owing to their extreme inherent hardness and the sliding surface areas of both scissor blades from becoming worn down as a result. As a negative consequence of the wear the initial tension of the scissors decreases in an undesired manner in the course of time. The wear in the area of the cutting edges is indeed reduced, in particular, by applying a hard material coating to both cutting edges and both sliding surface areas, but it is increased at the sliding surface areas. The present invention remedies this by the two sliding surface areas that slide along each other having different surfaces. Owing to the one sliding surface area having a surface provided with a hard material coating, and the other sliding surface area having a first hard material coating-free surface, the two sliding surface areas can no longer affect each other mutually, whereby wear of the sliding surface areas is minimized. As a positive consequence of this, the initial tension of the scissors is maintained for a longer time than with known scissors, so that all in all the service life of the scissors is increased.

The service life of the scissors may be further increased by both sliding surface areas having a hard material coating-free surface. It can thus be avoided that in the most unfavorable case a surface with a hard material coating and a surface without a hard material coating, which do not have good sliding properties, will encounter each other.

Furthermore, in the case of scissors of the kind described at the outset, it may be advantageous for at least one of the two sliding surface areas to have a surface provided with a hard material coating, which is polished smooth. Such a design makes it possible for the entire scissors, i. e., all its surfaces, to be provided with a hard material coating. An increased service life is achieved in that owing to the smooth polishing of the hard material coating a decrease in friction is achieved in at least one of the two sliding surface areas and wear is thereby reduced when using the scissors. It would also be conceivable to provide the other sliding surface area with a hard material coating-free surface.

It is expedient for both sliding surface areas to have a surface provided with a hard material coating, which is polished smooth. If, for example, the entire scissors are provided with a hard material coating, wear can then be further minimized when both sliding surface areas have a surface of particularly high quality owing to the smooth polishing of the hard material coating. Both friction and wear are thereby avoided and the service life of the scissors increased.

In accordance with a further preferred embodiment of the invention, it can be provided that the two scissor blades are held together by a connecting screw having a screw head and defining the pivot axis, that the scissor blade contacting an underside of the screw head forms a contact surface corresponding substantially to the shape and surface of the underside, and that the contact surface has a second hard material coating-free surface or a surface which has a hard material coating and is polished smooth. This design has the advantage that wear of the scissor blade sliding along the underside of the screw head is additionally reduced, with the positive consequence that the initial tension of the scissors is maintained for a longer time. This, in turn, results in prolongation of the service life, so that cost-intensive servicing and regrinding phases are considerably prolonged.

It is expedient for at least one of the two cutting edges to be made of a hard metal. Preferably, both cutting edges are made of a hard metal. It is particularly easy for scissor blades with such cutting edges to be provided with a hard material coating by chemical vapor deposition. In addition, they insure a basic hardness of the cutting edges and hence a minimum stability of the scissors.

It is advantageous for the hard material coating to be titanium-nitride (TiN), titanium-carbon-nitride (TiCN), titanium-aluminium-nitride (TiAlN) or a diamond-like carbon (DLC) coating. In particular, one sliding surface area and one or even both of the cutting edges can be provided with the hard material coating. It would also be possible to provide both scissor portions completely with a hard material coating, and the same or also a different hard material coating would be conceivable for both scissor portions. The aforementioned examples for hard material coatings do not constitute an exclusive list. In principle, other kinds of hard material coatings are also possible. The aforementioned single or multiple coatings increase the service life many times over in comparison with uncoated scissors and thus increase the thermal and also the chemical stability with hardnesses which clearly exceed those of hardened steel.

The friction and hence the wear of parts of the scissors sliding along one another is further reduced when the one first and/or the one second hard material coating-free surface has a high surface quality. In particular, when the aforementioned surfaces are particularly smooth, friction is minimized, irrespective of how the further surface sliding along the hard material coating-free surface is coated.

It is advantageous for the one first and/or the one second hard material coating-free surface to be produced by removing a hard material coating and high-gloss polishing the one scissor blade. In particular, in the case of scissor blades completely provided with a hard material coating, a wear-reducing sliding surface area can thus be produced in a simple way. The scissor blade can be completely provided with the hard material coating in a first operation and then worked on at the sliding surface area in a second operation by the hard material coating being removed at this point and the scissor blade being high-gloss polished.

It is also conceivable to reduce the friction by the one first and/or the one second hard material coating-free surface being formed by a slide layer applied to the one scissor blade. This has the advantage that a hard material coating need not necessarily be removed, but the slide layer can be applied directly.

The slide layer expediently comprises a ceramic material. A ceramic material is particularly wear-resistant and can be applied, for example, in the form of a lamina, in particular, by adhesive bonding to the scissor blade. Insertion of the ceramic material with positive locking in a corresponding recess of the scissor blade would also be conceivable.

The slide layer is preferably applied to the scissor blade in the form of a lamina forming the one sliding surface area. This makes it possible to produce the scissor blades in a simple way, and to select the sliding surface area or its surface individually in dependence upon the chosen hard material coating and to apply it to the one scissor blade.

In accordance with a preferred embodiment of the invention it can be provided that the slide layer is formed by a slide layer material which is adapted to be welded on and polished after the welding-on and which is polished after the slide layer material has been applied. This has the advantage that the slide layer is joinable even optimally to the scissor blade. In any case, it is made significantly more difficult for the slide layer or its surface to become detached from the scissor blade.

In addition, after application of the slide layer, it can, if required, be worked on and given a desired shape.

Manufacture of the scissors is further simplified when the slide layer material is steel. Steel can be welded on particularly well.

It is advantageous for the first hard material coating-free surface of the one sliding surface area to extend fully or substantially fully over an inner side of the one scissor blade, which includes the sliding surface area with the hard material coating-free surface and points in the direction towards the other scissor blade. This simplifies manufacture of the scissors. For example, the entire inner surface can be covered prior to coating the scissor blade. It would also be conceivable to cover only the sliding surface area prior to application of the hard material coating. Furthermore, this also has the advantage that the cutting edges can in a simple way have different surfaces. In particular, when using the scissors as electrosurgical instrument, a current can then be conducted via one scissor blade, for example, and the two cutting edges can be electrically insulated from each other.

The design of the scissors is further simplified when the shape of the sliding surface area with the first hard material coating-free surface is substantially rectangular. In addition, in the case of scissors otherwise completely provided with a hard material coating, the hard material coating-free surface can in this way be minimized, so that the scissor blades are protected particularly well, for example, against aggressive chemicals.

It is expedient for the shape of the second hard material coating-free surface to be substantially annular. In this way, only a minimal surface has to be made hard material coating-free. Since, in particular, the part of the screw head lying against the scissor blade is annular, an annular hard material coating-free surface is, therefore, adequate to minimize the wear between the connecting screw and the scissor blade lying against it.

The scissors as a whole are optimally protected against outer influences, in particular, against aggressive chemicals, when the entire scissors are provided with the hard material coating except for the sliding surface area having a hard material coating-free surface. In addition, this makes it possible to dye scissor blades made of hard metal in a desired manner. For example, a titanium-nitride coating forms a gold-colored surface, a titanium-carbon-nitride coating a violet/gray surface, a titanium-aluminium-nitride coating a blue/gray surface and a diamond-like carbon coating (DLC) a dark gray surface. Thus, the scissors may, for example, be dyed in accordance with the purpose for which they are to be used, without having to forgo the advantages of a hard material coating.

In accordance with a further preferred embodiment of the invention, it can be provided that the one scissor blade is completely or substantially completely provided with the hard material coating, and that the other scissor blade is completely made of a material having a hard material coating-free surface. This design makes it possible to select an optimum material combination for both scissor blades in accordance with the purpose for which the scissors are to be used. Furthermore, only one of the two scissor blades need be coated, which helps to reduce both the manufacturing expenditure and the manufacturing costs.

It is expedient for the material from which the other scissor blade is made to be a ceramic material or a high-gloss polished metal with a hard metal insert.

In particular, in order to identify the type of scissors and to reduce wear thereof by an operator, it may be advantageous for the connecting screw and/or eye rings of the scissors arranged at proximal ends of the scissor blades to be gold-plated or provided with a titanium-nitride (TiN) coating.

The object stated at the outset is accomplished with a method of the kind described at the outset for the manufacture of surgical scissors, in accordance with the invention, by a surface of at least one sliding surface area being manufactured so as to be hard material coating-free. As described above, in this way wear of the sliding surface areas sliding along each other is minimized, whereby the initial tension of the scissor blades movably mounted on each other can be maintained for a particularly long time.

Wear can be further minimized by both sliding surface areas being manufactured so as to be hard material coating-free. Thus, two hard material coating-free sliding surface areas can slide along each other when the scissors are opened and closed, which minimizes both friction and wear.

Furthermore, it is advantageous when in a method of the kind described at the outset a surface of at least one sliding surface area is provided with a hard material coating, and when this surface is polished smooth after application of the hard material coating. Smooth polishing of the hard material coating results in a high-quality surface, which has a wear- and friction-reducing effect when the sliding surface areas slide along each other. This can also increase the service life of the scissors. It would be conceivable to make the other sliding surface area hard material coating-free. It is also advantageous for surfaces of both sliding surface areas to be provided with a hard material coating and for the surfaces to be polished smooth after application of the hard material coating. In this way, wear of the sliding surface areas is further minimized and, therefore, the service life of the scissors further increased.

The method can be further improved in a simple way when the entire scissors or substantially the entire scissors are provided with a hard material coating, and when the hard material coating of the surface of the other sliding surface area is removed by polishing.

It is advantageous for the surface of the other sliding surface area to be covered prior to application of the hard material coating to the scissors. In particular, in the case of a hard material coating which is very hard, the removal of the hard material coating after its application by grinding or polishing can involve a great deal of expenditure. Therefore, the covering of the sliding surface area allows only those surface areas of the scissor blade or blades which are to be provided with a hard material coating, for example, by chemical vapor deposition, to be provided with such a coating.

It is expedient for the two scissor blades to be held together by a connecting screw comprising a screw head and defining the pivot axis, for the scissor blade contacting an underside of the screw head to form a contact surface corresponding substantially to the shape and surface of the underside, and for the surface of the contact surface to be manufactured so as to be hard material coating-free or to be provided with a hard material coating and subsequently polished smooth. Wear in the area of the pivot axis between the connecting screw and the scissor blade contacting it is thereby minimized, so that the initial tension of the scissors is maintained longer, which results in a significantly prolonged service life of the scissors.

In order to give the scissors a uniform appearance and also to protect them as a whole particularly well against outer influences, in particular, aggressive chemicals or the like, it is expedient for the entire scissors or substantially the entire scissors to be provided with a hard material coating, and for the hard material coating of the surface of the contact surface to be removed by polishing. It is particularly simple to manufacture the scissors in this way.

It is advantageous for the surface of the contact surface to be covered prior to application of the hard material coating to the scissors. In this way, one method step in the manufacture of the scissors can be dispensed with, namely removal of the hard material coating of the surface of the contact surface by grinding or polishing after application of the hard material coating, for example, by chemical vapor deposition.

It is particularly easy and quick for an operator to recognize the type of scissors when the connecting screw and/or eye rings of the scissors arranged at proximal ends of the scissor blades are gold-plated or provided with a titanium-nitride (TiN) coating. Furthermore, corrosion of the correspondingly coated parts of the scissors, which may occur, in particular, when cleaned or used by an operator, can be prevented.

The following description of preferred embodiments of the invention serves in conjunction with the drawings to explain the invention in greater detail.

DETAILED DESCRIPTION OF THE INVENTION

Figure 1:
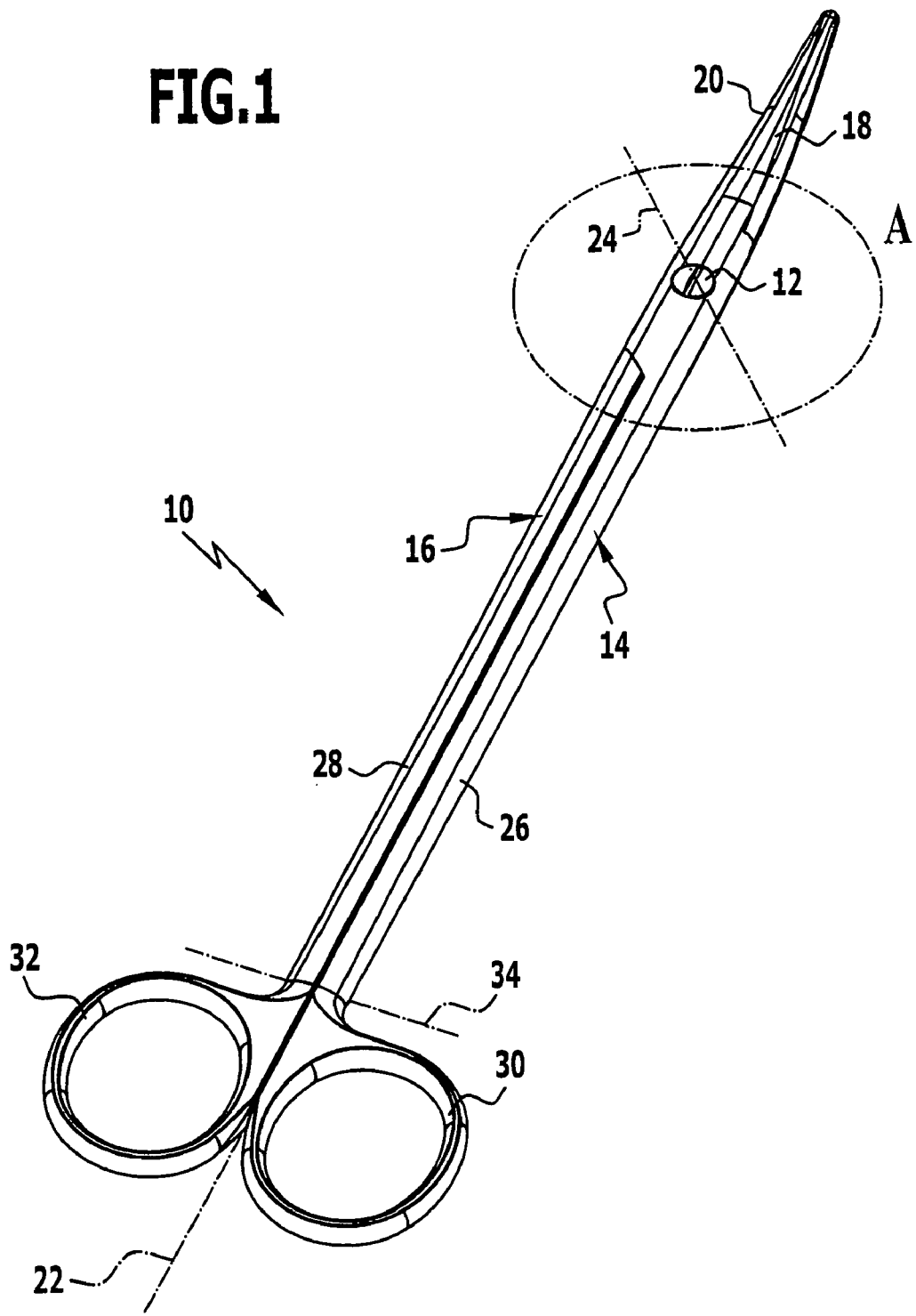
FIG. 1 is a perspective view of scissors according to the invention in the closed state.
Figure 2:
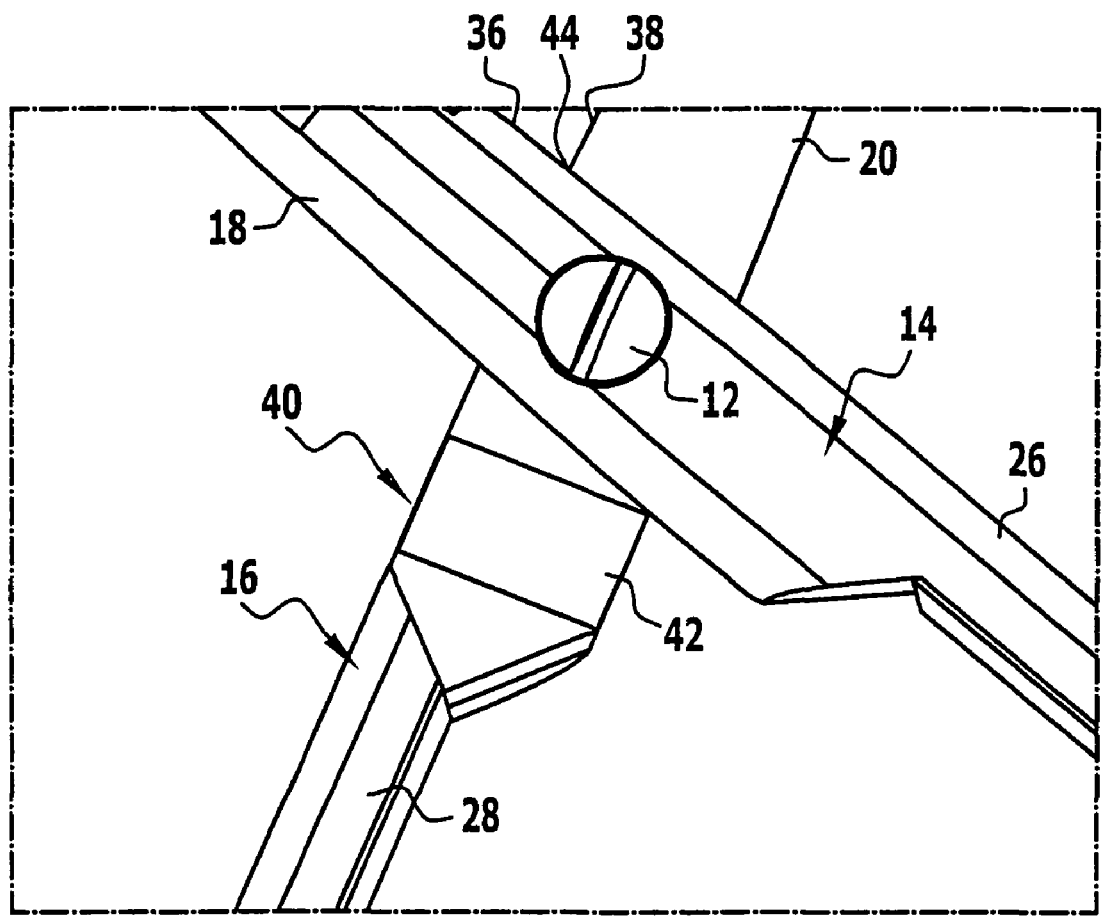
FIG. 2 is an enlarged view of area A in FIG. 1 with scissor blades in the open state.

FIG. 1 shows surgical scissors generally designated by reference numeral 10 with two scissor halves, namely the upper scissor portion 14 and the lower scissor portion 16, mounted pivotably on each other by means of a connecting screw 12.

Scissor blades 18 and 20 of the upper scissor portion 14 and the lower scissor portion 16, respectively, are curved in a direction pointing away from a longitudinal axis 22 of the scissors 10. At the proximal side of the connecting screw 12, which defines a pivot axis 24, elongate shafts 26 and 28 of the upper scissor portion 14 and the lower scissor portion 16, respectively, extend parallel to each other and abuttingly on each other when the scissors 10 are closed. Eye rings 30 and 32, which are gold-plated up to a boundary line 34, adjoin proximal ends of the shafts 26 and 28. The connecting screw 12 is also gold-plated.

Apart from the eye rings 30 and 32 and the connecting screw 12, both upper scissor portion 14 and lower scissor portion 16 of the scissors 10 are provided with a hard material coating of titanium-aluminium-nitride. In particular, this serves to reduce wear at cutting edges 36 and 38 of the scissor blades 18 and 20. However, in order to also reduce the wear in the so-called "between" (intermediate portion) 40 of the scissors 10, there is provided at the proximal side of the pivot axis 24 on the upper scissor portion 14 and also on the lower scissor portion 16 a sliding surface area 42 of substantially rectangular shape, which is free of a coating of hard material. Upon opening and closing the scissors 10, upper scissor portion 14 and lower scissor portion 16 contact each other not only at a moving point of contact 44 of the cutting edges 36 and 38 sliding along each other, but also in the between 40, more specifically, in the hard material coating-free sliding surface area 42 of the lower scissor portion 16 and in the hard material coating-free sliding surface area 42 of the upper scissor portion 14, which is not apparent from the drawings. As a result of removing the coating of hard material in the sliding surface area 42 different surfaces slide along one another upon opening and closing the scissors 10.

If both sliding surface areas 42 were provided with a hard material coating, these could then mutually act as abrasive surfaces, if affected in some form or other, and additionally cause wear in the between 40, which would cause the initial tension of the scissors 10 to be reduced. If the lower scissor portion 16 is first provided with a hard material coating, the sliding surface area 42 can then be formed by grinding and subsequent high-gloss polishing. A high-quality surface is thus obtained.

Alternatively, the sliding surface area 42 can be covered before applying the hard material coating. The coating of hard material may, for example, be produced by chemical vapor-phase deposition. It would also be conceivable to not completely remove the hard material coating on one or both of the sliding surface areas 42, but to only polish smooth the rough surface of the coating. Instead of removing a previously applied hard material coating, the sliding surface area 42 can also be formed by applying a ceramic part or a material applied, for example, by welding.

Figure 3:
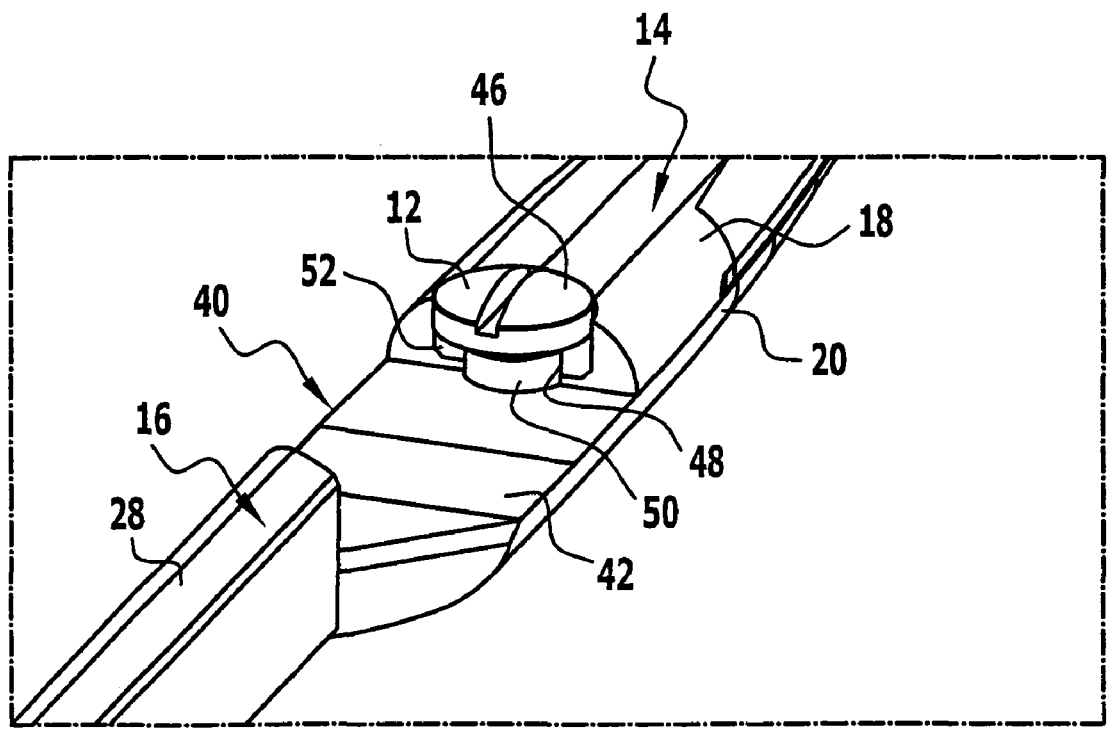
FIG. 3 is a partially sectional view of the scissors from FIG. 1 in the area A.

A further area of the scissors 10 that is susceptible to wear is shown in FIG. 3. With its threaded section 50 screwable to the lower scissor portion 16, the connecting screw 12 extends through a bore 48 tapering in a single step in the direction towards the lower scissor portion 16, so that a head 46 of the connecting screw 12 can be countersunk almost completely in the upper scissor portion 14. To minimize friction between the head 46 of the connecting screw 12 and the upper scissor portion 14 upon opening and closing the scissors, a ceramic ring 52 is inserted into the bore 48 tapering in the form of a single step, so that an underside of the head 46 is in contact with the ceramic ring 52, whereby friction is reduced when the scissor blades 18 and 20 are pivoted relative to each other. This reduces the wear and thus maintains the initial tension of the scissors 10. Instead of a ceramic ring 52, a different friction-reducing material in the form of a ring may also be inserted or applied, or a previously applied coating of hard material can be completely removed or polished smooth.

Figure 4:
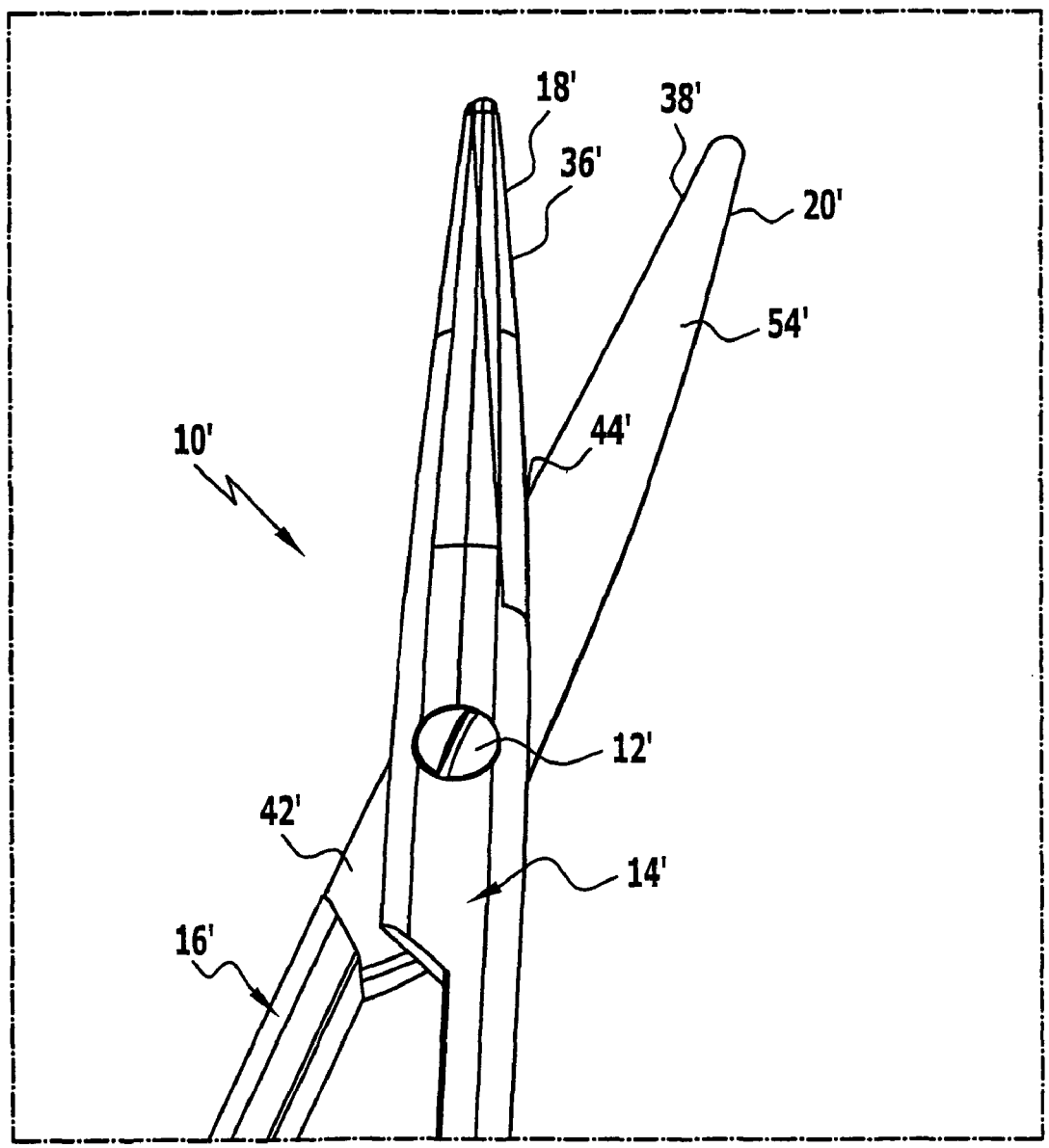
FIG. 4 shows a distal end of a second embodiment of scissors according to the invention.

A second embodiment of scissors generally designated by reference numeral 10' is shown in FIG. 4. Parts of the scissors 10', which are identical or similar to parts of the scissors 10, are given the same reference numerals, but with an additional prime ('). The scissors 10' differ from the scissors 10 in that an inner side 54' of the scissor blade 20' of the lower scissor portion 16' is completely free of hard material coating. This means that the sliding surface area 42' is part of the inner side 54'. The inner side 54' can be formed either by grinding a previously applied hard material coating and by applying a wear-reducing material, for example, in the form of a ceramic lamina, or by applying, in particular by welding, a hard steel which can be machined, in particular, by high-gloss polishing, after being applied.

In connection with the description of a third embodiment, reference can again be had to FIG. 1 for an illustration. Differently from the scissors 10, upper scissor portion 14 and lower scissor portion 16 of the third embodiment are, however, made of different materials. For example, the lower scissor portion 16 can be made from a hard steel and provided in its entirety with a hard material coating, whereas the upper scissor portion 14 can be made entirely from a ceramic material or from any chosen material and can have a surface which is completely free of hard material coating. The sliding surface area 42 of the lower scissor portion 16 can be machined, for example, by removing the hard material coating or formed by polishing the coating smooth.

All three embodiments of scissors according to the invention described herein have in common that both sliding surface areas 42 have a high-quality smooth surface for the reduction of friction and wear.

The invention claimed is:

1. Surgical scissors, comprising:
   two scissor blades, each of which is made entirely of the same steel material, said scissor blades being mounted for pivotal movement relative to each other about a pivot axis and having one cutting edge each,
   said scissor blades having proximally of the pivot axis one steel sliding surface area each, said steel sliding surface areas sliding along each other and said scissor blades contacting each other distally of the pivot axis at a moving point of contact of the cutting edges sliding along each other when the scissors are opened and closed, and
   at least one of the cutting edges being provided with a hard material coating, wherein:
   the two steel sliding surface areas have a first hard material coating-free surface comprising said steel material of said corresponding scissor blade; and
   the entire scissor blades are provided with the hard material coating except for the steel sliding surface areas having the hard material coating-free surface.

2. Scissors in accordance with claim 1, wherein:
   the two scissor blades are held together by a connecting screw having a screw head and defining the pivot axis,
   an area of one of the scissor blades in contact with an underside of the screw head forms a contact surface corresponding substantially to a shape and surface of the underside of the screw head, and
   the contact surface has a second hard material coating-free surface or a surface which has a hard material coating and is polished smooth.

3. Scissors in accordance with claim 2, wherein at least one of the first and the second hard material coating-free surface has a high surface quality.

4. Scissors in accordance with claim 2, wherein at least one of the first and the second hard material coating-free surface is produced by removing a hard material coating and high-gloss polishing the scissor blades.

5. Scissors in accordance with claim 2, wherein a shape of the second hard material coating-free surface is substantially annular.

6. Scissors in accordance with claim 1, wherein at least one of the two cutting edges is made of a hard metal.

7. Scissors in accordance with claim 1, wherein the hard material coating is titanium-nitride (TiN), titanium-carbon-nitride (TiCN), titanium-aluminium-nitride (TiAlN) or a diamond-like carbon (DLC) coating.

8. Scissors in accordance with claim 1, wherein the first hard material coating-free surface of the sliding surface areas extends fully or substantially fully over an inner side of the scissor blades, each of which includes the sliding surface area with the hard material coating-free surface and points in a direction towards the other scissor blade.

9. Scissors in accordance with claim 1, wherein a shape of the sliding surface areas with the first hard material coating-free surface is substantially rectangular.

10. Scissors in accordance with claim 1, wherein a connecting screw and/or eye rings of the scissors arranged at proximal ends of the scissor blades are gold-plated or provided with a titanium-nitride (TiN) coating.

11. Method for the manufacture of surgical scissors, comprising:

mounting two scissor blades for pivotal movement relative to each other about a pivot axis, each of said scissor blades being made entirely of the same steel material, providing each scissor blade with one cutting edge each, said scissor blades having proximally of the pivot axis one steel sliding surface area each, said steel sliding surface areas sliding along each other and said scissor blades contacting each other distally of the pivot axis at a moving point of contact of the cutting edges sliding along each other when the scissors are opened and closed, and providing at least one of the cutting edges with a hard material coating, wherein:

surfaces of the two steel sliding surface areas are manufactured so as to be hard material coating-free; and the entire scissor blades are provided with the hard material coating except for the steel sliding surface areas having a hard material coating-free surface comprising said steel material of said corresponding scissor blade.

12. Method in accordance with claim 11, wherein:

the two scissor blades are held together by a connecting screw comprising a screw head and defining the pivot axis, an area of one of the scissor blades in contact with an underside of the screw head forms a contact surface corresponding substantially to a shape and surface of the underside of the screw head, and the contact surface is manufactured so as to be hard material coating-free or is provided with a hard material coating and subsequently polished smooth.

13. Method in accordance with claim 12, wherein the surface of the contact surface is covered prior to application of the hard material coating to the scissors.

14. Method in accordance with any claim 12, wherein at least one of the connecting screw and eye rings of the scissors arranged at proximal ends of the scissor blades are gold-plated or provided with a titanium-nitride (TiN) coating.

\* \* \* \* \*